United States Patent [19]

Shorr

[11] Patent Number: 5,900,402
[45] Date of Patent: May 4, 1999

[54] METHOD OF REDUCING SIDE EFFECTS ASSOCIATED WITH ADMINISTRATION OF OXYGEN-CARRYING PROTEINS

[75] Inventor: Robert G. L. Shorr, Edison, N.J.

[73] Assignee: Enzon, Inc., Piscataway, N.J.

[21] Appl. No.: 08/865,035

[22] Filed: May 29, 1997

[51] Int. Cl.⁶ .......................... A01N 37/18; A61K 38/16; C07K 14/00; C07K 16/00
[52] U.S. Cl. .................... 514/6; 514/2; 530/385
[58] Field of Search ............................ 514/2, 6; 530/385

[56] References Cited

U.S. PATENT DOCUMENTS

| | | | |
|---|---|---|---|
| 5,028,588 | 7/1991 | Hoffman et al. | 408/30 |
| 5,079,337 | 1/1992 | Leonard et al. | 408/30 |
| 5,234,903 | 8/1993 | Nho et al. | 408/30 |
| 5,312,808 | 5/1994 | Shorr et al. | 408/30 |
| 5,321,095 | 6/1994 | Greenwald | 408/30 |
| 5,324,844 | 6/1994 | Zalipsky | 408/30 |
| 5,349,001 | 9/1994 | Greenwald et al. | 408/30 |
| 5,386,014 | 1/1995 | Nho et al. | 408/30 |
| 5,478,805 | 12/1995 | Shorr et al. | 408/30 |
| 5,599,907 | 2/1997 | Anderson et al. | 408/30 |
| 5,605,976 | 2/1997 | Martinez et al. | 408/30 |
| 5,658,879 | 8/1997 | Nho | 408/30 |

FOREIGN PATENT DOCUMENTS

| | | |
|---|---|---|
| WO95/11924 | 5/1995 | WIPO . |
| WO96/00080 | 1/1996 | WIPO . |

OTHER PUBLICATIONS

Looker, D. et al., "A Human Recombinant Haemoglobin Designed For Use as a Blood Substitute", Mar. 19, 1992; vol. 356, pp. 258–260.

Winslow, R. M., et al. Physiologic Effects of Hemoglobin–based Oxygen Carriers compared to Red Blood Cells in Acute Hemorrhage; Abstract #2494, p. 626a, Blood vol. 88, No. 10. Supp. 1; Nov. 15, 1996.

Conover, C.D., et al. The Effects of Hemodilution with Polyethylene Glycol Bovine Hemoglobin (PEG–Hb) in a Conscious Porcine Model; J. Investig. Med. 44:238–246; 1996.

Conover, C. D., et al. Physiological Effect of Polyethylene Glycol Conjugation on Stroma–Free Bovine Hemoglobin in the Conscious Dog After Partial Exchange Transfusion; Artificial Organs 21(5):369–378; 1997.

Conover, C.D., et al. Effect of Polyethylene Glycol Conjugated Bovine Hemoglobin in Both Top–Load and Exchange Transfusion Rat Models; Artificial Organs 21(10):1066–1075; 1997.

Conover, C.D., et al. The Influence of Polyethylene Glycol Conjugation on Bovine Hemoglobin's Intrinsic Effect on the Gastrointestinal System of the Rat; Life Sciences, vol. 59, No. 22;pp. 1861–1869; 1996.

Shum, K. L., et al. The Physiological & Histopathological Response of Dogs to Exchange Transfusion w/Polyethylene Glycol–Modified Bovine Hemoglobin; Art Cells Blood Subs and Immob Biotech; 24(6) pp. 655–683; 1996.

Song D., et al. Comparison of the Efficacy of Blood and Polyetylene Glycol–Hemoglobin in Recovery of Newborn Piglets from Hemorrhagic Hypotension: Effect on Blood Pressure . . . ; Transfusion vol. 35, No. 7, 552–558; 1995.

Shorr, R. G. L., et al. Polythylene Glycol Modified Hemoglobin: Effects on Blood Pressure and Heart Rate in the Canine; Abstract from Presentation at Experimental Biology 94 Convention; 1994.

*Primary Examiner*—Cecilia J. Tsang
*Assistant Examiner*—S. G. Marshall
*Attorney, Agent, or Firm*—Roberts & Mercanti, L.L.P.

[57] ABSTRACT

A method of reducing side-effects associated with administering oxygen-carrying proteins to mammals is disclosed. The method includes:

a) reacting an oxygen-carrying protein with a substantially non-antigenic polymer to form a oxygen-carrying protein-substantially non-antigenic polymer conjugate; and b) administering the oxygen-carrying protein-substantially non-antigenic polymer conjugate to a mammal in need of the oxygen-carrying protein. Preferred oxygen-carrying proteins include recombinantly prepared hemoglobins and preferred non-antigenic polymers include polyethylene glycol.

43 Claims, 8 Drawing Sheets

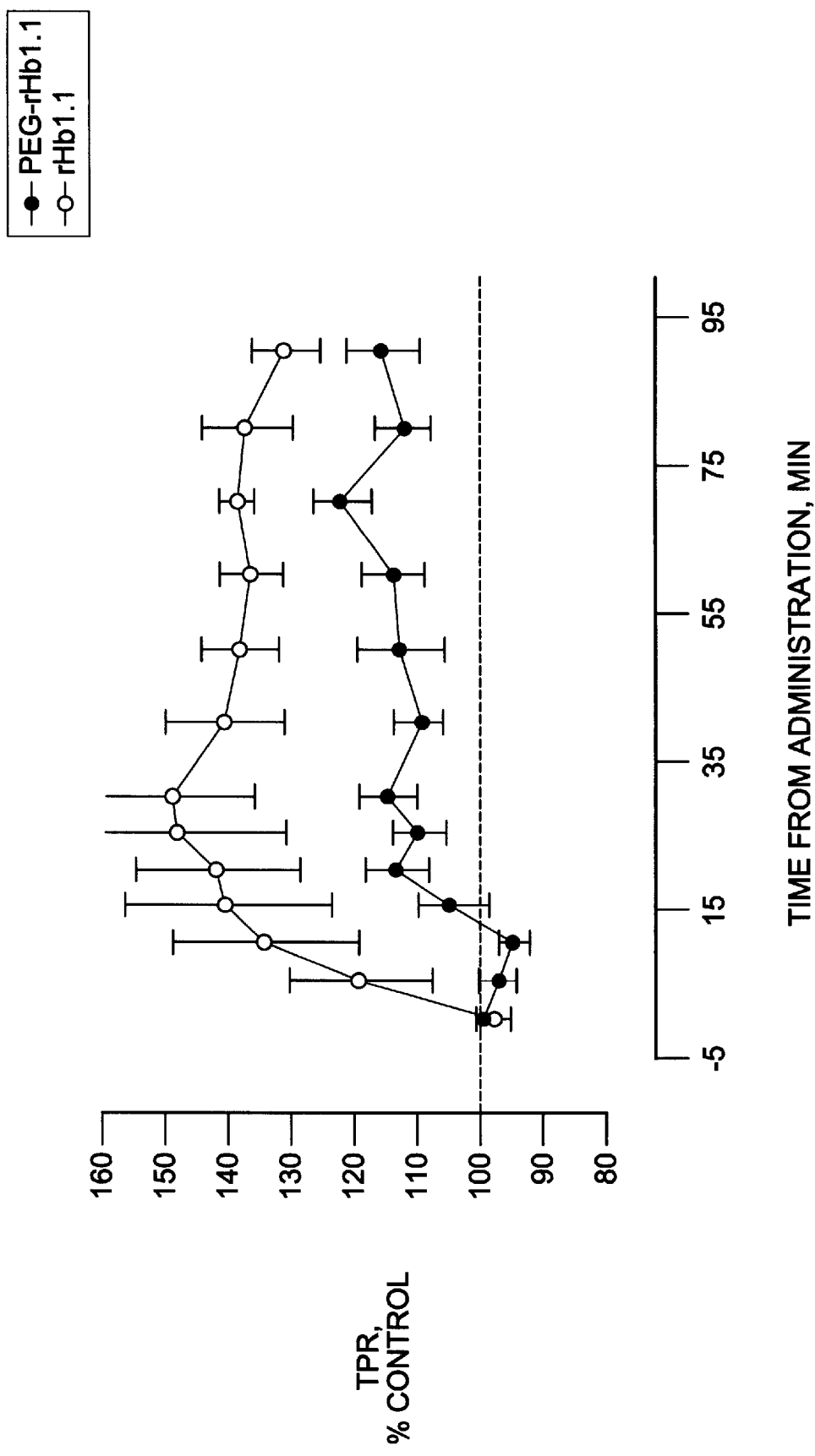

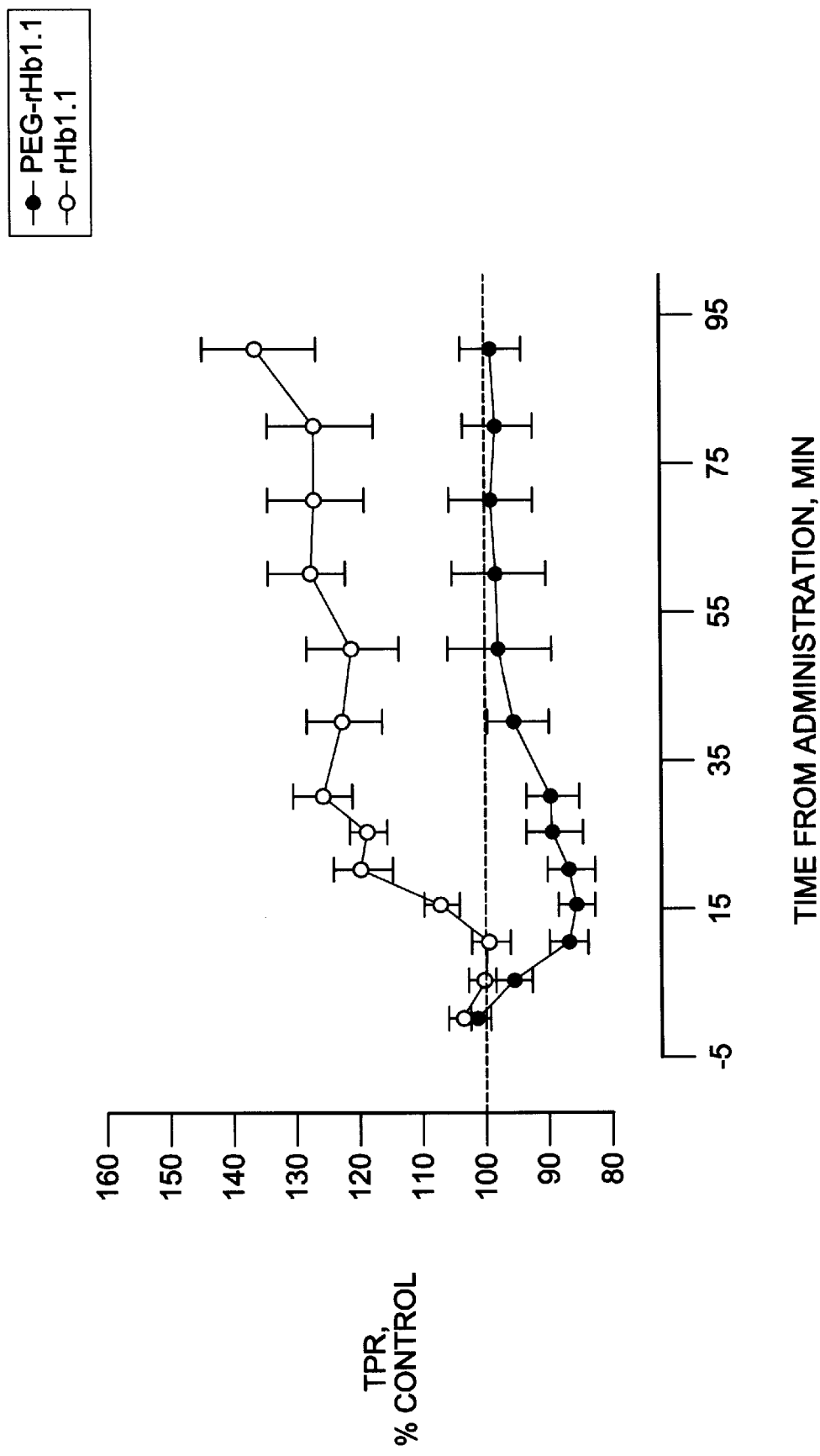

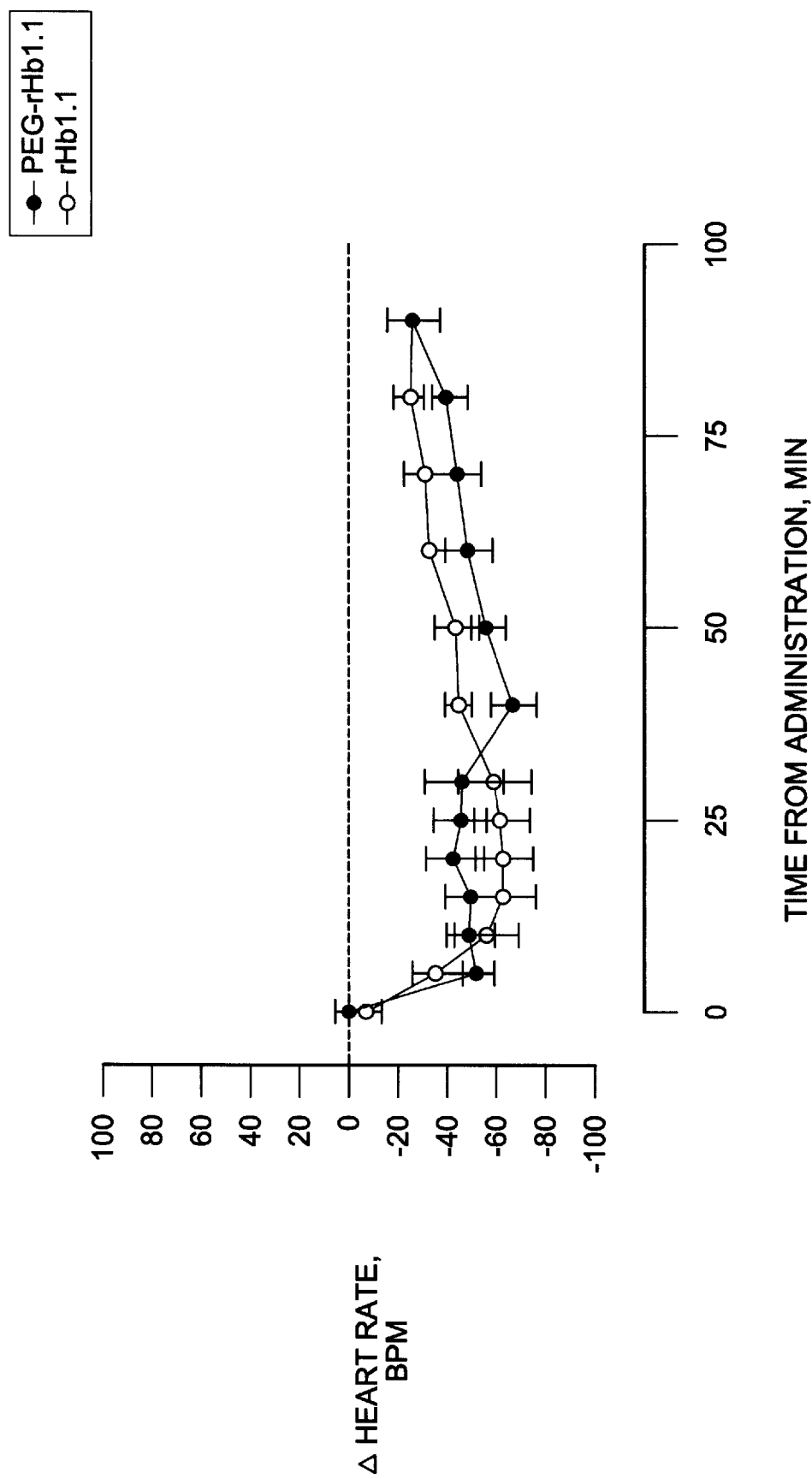
FIG-2a ΔHEART RATE 350 mg/kg

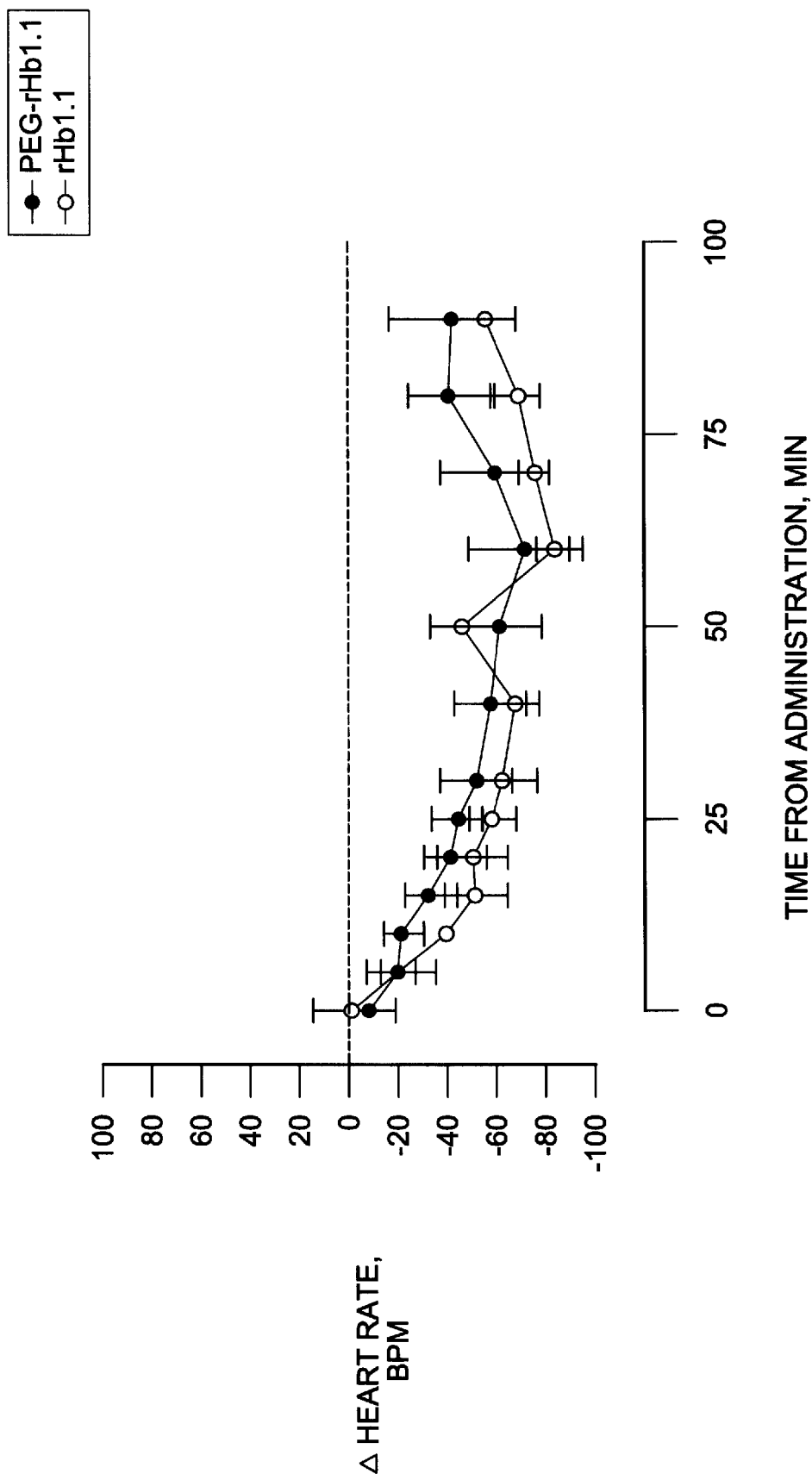

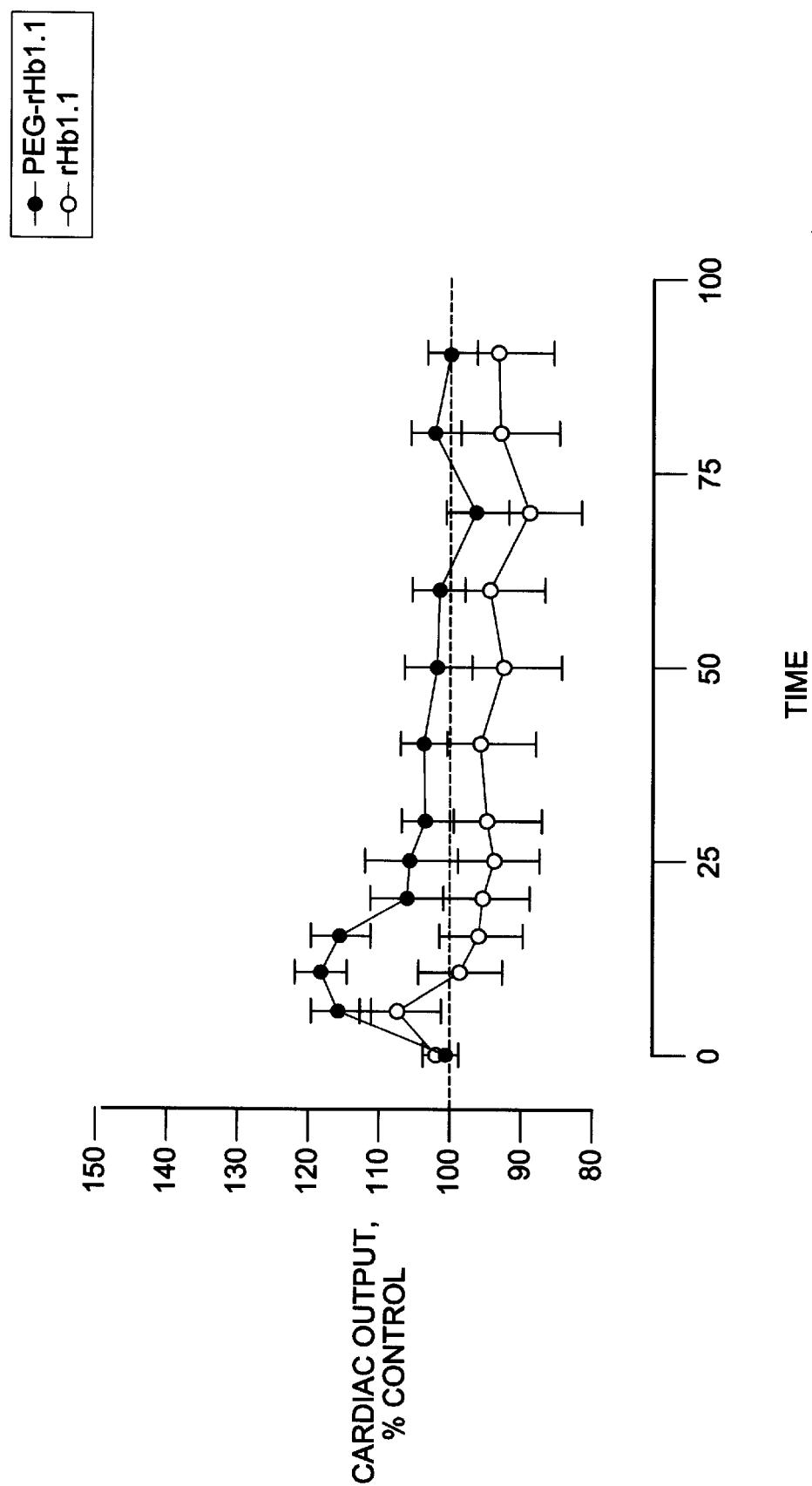
FIG-3a CARDIAC OUTPUT 350 mg/kg

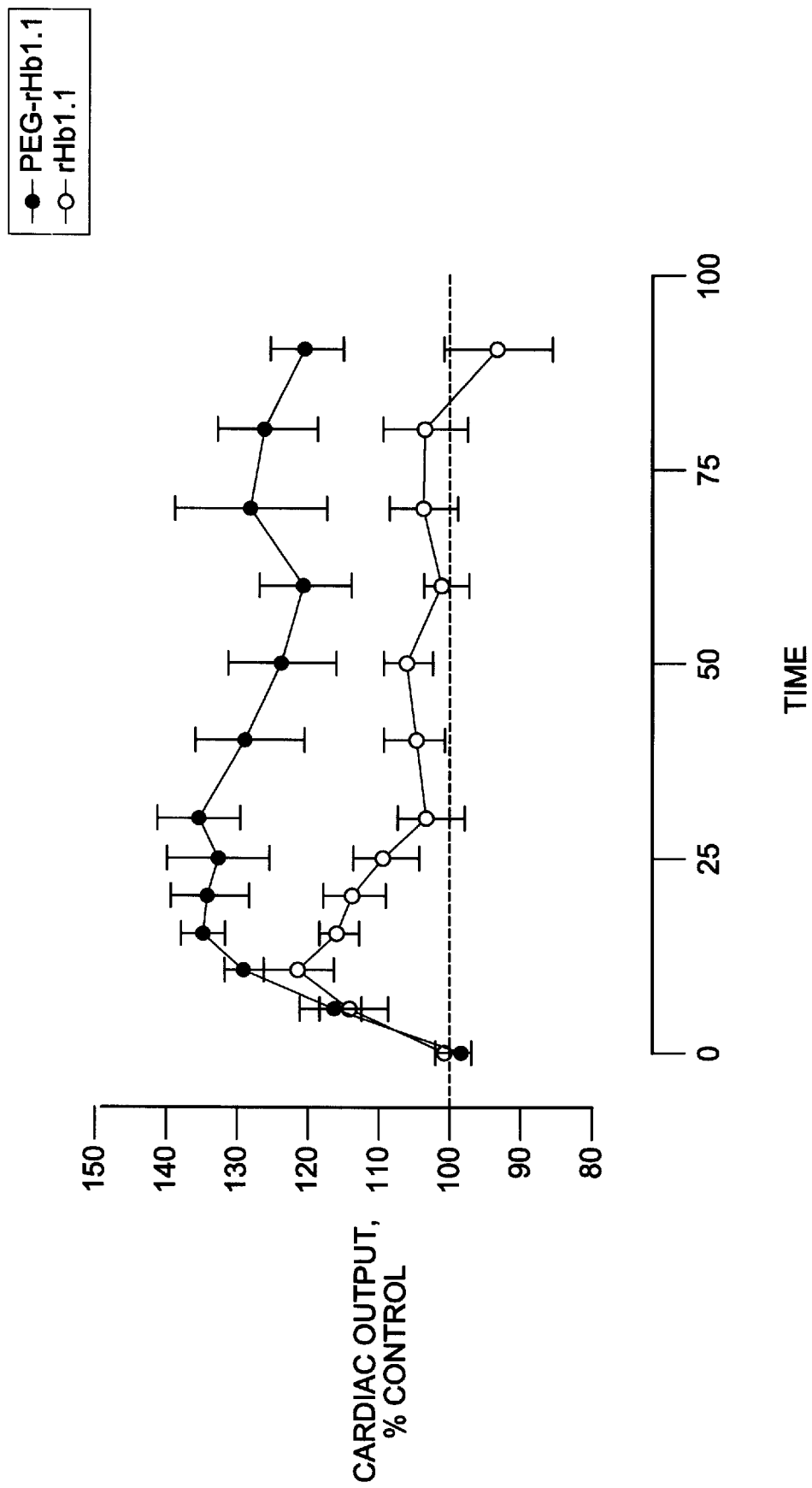

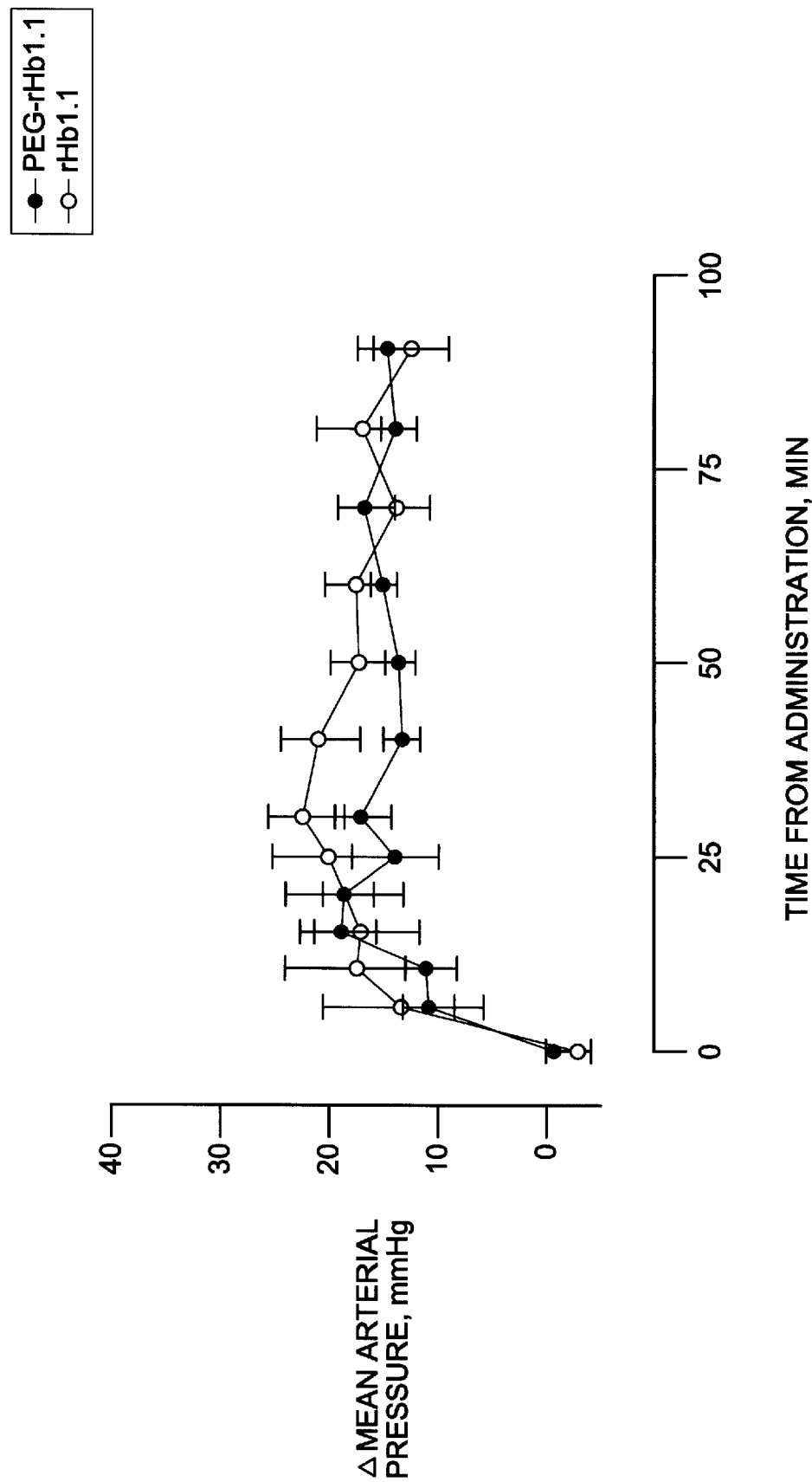
FIG-4a Δ MEAN ARTERIAL PRESSURE 350 mg/kg

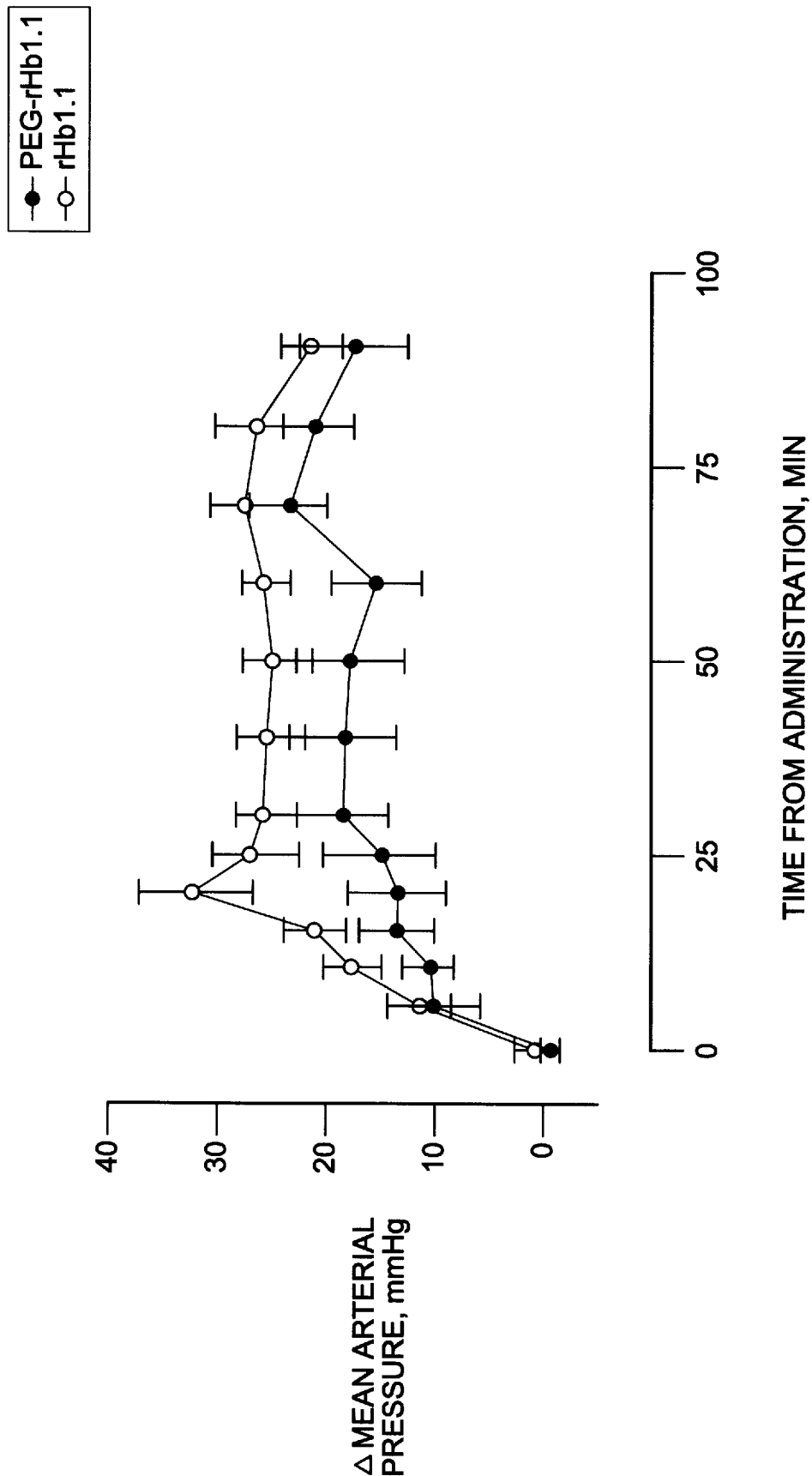

METHOD OF REDUCING SIDE EFFECTS ASSOCIATED WITH ADMINISTRATION OF OXYGEN-CARRYING PROTEINS

BACKGROUND OF THE INVENTION

1. Field of the Invention

The present invention relates to methods of reducing the side-effects associated with administering oxygen-carrying proteins to mammals. In particular, the present invention relates to methods of reducing the side-effects associated with administering hemoglobin-containing compositions to mammals in need thereof.

2. Description of Related Art

Over the years, several substances have been suggested as potential replacements for the naturally-occurring hemoglobin-based oxygen transport systems of mammals. For example, the scientific literature often includes reports of various blood substitutes such as perfluorocarbon emulsions, recombinant hemoglobin products, cross-linked hemoglobin compositions which include human or bovine hemoglobins, ultra-purified bovine hemoglobin compositions and polyethylene glycol-hemoglobin conjugates.

Not unexpectedly, there have been shortcomings associated with many of the products under consideration. For example, early perfluorocarbon emulsions have not been favorably accepted due to drawbacks associated with product preparation before use (dilution and mixing), detergent based-emulsifying agents and the requirement that the patient breathe 95% oxygen during use. In addition, the compounds have a short circulating life, and are known to accumulate in the liver and spleen. The product is not metabolized per se but rather is exhaled as a gas over time through the lungs. Given the prolonged organ residence time, toxicities including thrombocytopenia have raised concerns regarding multiple doses and tissue loading.

In addition, the (in vivo) circulating life of some blood substitutes has been less than that which is believed to be therapeutically optimal. Some solutions have been offered to address this shortcoming. For example, inter- and/or intra-molecular cross-linking hemoglobin molecules or covalently attaching polymers such as PEG have been suggested as means for extending the circulating life of the oxygen carriers. See also U.S. Pat. Nos. 5,234,903, 5,386,014, 5,312,808 and 5,478,805, the contents of which are each incorporated herein by reference.

Some proposed products have been associated with significant side-effects after intravenous administration. Side-effects, if significant, substantially reduce the commercial and therapeutic value of these products. For example, some recombinant hemoglobin products undergoing clinical evaluation were found to unexpectedly cause alpha-adrenergic, acetylcholine-mediated, possible endothelin and/or nitric oxide-induced side effects in humans after administration. These side-effects are believed to be related to not only the dose of the recombinant hemoglobin administered but also the formulation of the recombinant hemoglobin and volume administered. Current recombinant hemoglobin formulations under consideration, therefore, are of limited usefulness especially in situations where large amounts of the recombinant protein are required for treatment. Large volume administration of such preparations for replacement of blood loss due to trauma or transfusions are likely to result in one or more side-effects.

It would be highly desirable to provide a method of allowing oxygen-carrying proteins to be delivered to patients in relatively large volumes without significantly incurring the types of side-effects which heretofore were observed. The present invention addresses this issue and is described below.

SUMMARY OF THE INVENTION

The present invention provides methods of reducing side-effects associated with administering oxygen-carrying proteins to mammals. In accordance therewith, the methods include:

a) reacting an oxygen-carrying protein with a substantially non-antigenic polymer to form an oxygen-carrying protein-substantially non-antigenic polymer conjugate; and b) administering the resultant conjugate to a mammal in need of a treatment which includes oxygen-carrying proteins. As a result of these methods, a significant reduction in the side-effects associated with the administration of the unconjugated oxygen-carrying protein is observed.

In a preferred aspect of the invention, the oxygen-carrying protein is a recombinantly-prepared hemoglobin such as rHb1.1, a mutant pseudotetrameric di-alpha-cross-linked-hemoglobin. Additional suitable hemoglobins include other recombinant hemoglobins such as wild type or mutant mammalian hemoglobins. Non-recombinantly-prepared mammalian hemoglobins such as human or ruminant hemoglobins can also be used. Other embodiments include non-hemoglobin-based oxygen carrier proteins such as eukaryotic or prokaryotic flavo(hemoglobin) proteins, cyanohemoglobins or hemerythrins, which are capable of carrying oxygen.

In another aspect of the invention there is provided a substantially non-tissue penetrating hemoglobin-based formulation. The formulation includes a hemoglobin conjugated with or encapsulated in a suitable carrier such as a substantially non-antigenic polymer or liposome. The conjugates or encapsulates have a molecular weight of at least about 120,000 daltons and preferably at least about 130,000 daltons. For purposes of the present invention, "non-penetrating" is to be understood to mean that the hemoglobin portion of the compositions substantially avoid entrance or penetration into the tissue sites necessary for nitric oxide scavenge.

The substantially non-antigenic polymer portion of the conjugates is preferably a poly(alkylene oxide) and more preferably, a poly(ethylene glycol). The conjugates are administered to a mammal as part of pharmaceutically-acceptable fluids or solutions as such terms are understood in the art. Prior to administration, the pharmaceutically-acceptable solutions contain from about 0.2 to about 40 wt. % conjugates. In the case of PAO-Hb conjugates, it will be appreciated that the conjugates are composed of about 50% Hb by weight.

The amount of non-antigenic polymer attached to the oxygen-carrying protein is generally described as an amount which is sufficient to significantly reduce the side effects observed when the unconjugated oxygen carrier is administered to a similarly treated mammal. The amount will be dependent on several factors including the preferences of the artisan, the type of oxygen-carrying protein selected for modification, the type of polymer used for conjugation, the molecular weight of the polymer and other requirements which will be apparent to the artisan.

The present invention has several advantages over the prior art. It has unexpectedly been found that the covalent attachment of the polymer to recombinantly-prepared hemoglobins substantially reduces or even eliminates the side-effects which have limited their therapeutic use in mammals. For example, after administration of the polymer-conjugated recombinant hemoglobin composition, vasoconstriction is substantially less than that observed with unconjugated recombinant hemoglobin compositions. Furthermore, the alterations in gastrointestinal function which have been observed after administration of the unconjugated recombinant hemoglobin products are also substantially reduced. While Applicant is not bound by theory, it is believed that the unexpected improvements in the side-effect profile of the recombinant hemoglobin conjugate are unrelated to the previously observed properties and benefits associated with covalent polymer conjugation, i.e. increased circulating life, improved solubility and reduced antigenicity.

For a better understanding of the present invention, reference is made to the following detailed description, and its scope will be pointed out in the appended claims.

BRIEF DESCRIPTION OF THE DRAWINGS

FIG. 1a graphically illustrates total peripheral resistance after i.v. administration of 350 mg/kg of PEG-rHb1.1 or an unconjugated recombinant hemoglobin composition designated rHb1.1.

FIG. 1b graphically illustrates total peripheral resistance after i.v. administration of 750 mg/kg of PEG-rHb1.1 or unconjugated rHb1.1.

FIG. 2a graphically illustrates the differences in heart rate after i.v. administration of 350 mg/kg of PEG-rHb1.1 or rHb1.1.

FIG. 2b graphically illustrates the differences in heart rate after i.v. administration of 750 mg/kg of PEG-rHb1.1 or rHb1.1.

FIG. 3a graphically illustrates the differences in cardiac output after i.v. administration of 350 mg/kg of PEG-rHb1.1 or rHb1.1.

FIG. 3b graphically illustrates the differences in cardiac output after i.v. administration of 750 mg/kg of PEG-rHb1.1 or rHb1.1.

FIG. 4a graphically illustrates the differences in mean arterial pressure after i.v. administration of 350 mg/kg of PEG-rHb1.1 or rHb1.1.

FIG. 4b graphically illustrates the differences in mean arterial pressure after i.v. administration of 750 mg/kg of PEG-rHb1.1 or rHb1.1.

DETAILED DESCRIPTION OF THE INVENTION

A. Introduction

In addition to the utility of PAO-Hb conjugates as a treatment for hypovolemia, shock, anemia and cancerous tumors, additional research has been conducted. It has been unexpectedly found that polymer conjugation of certain oxygen-carrying proteins, such as certain recombinant hemoglobin, can substantially reduce the side effects associated with the administration of certain oxygen carriers to mammals. For example, it was completely unexpected that covalent attachment of non-antigenic polymers to recombinantly-engineered $\alpha$-$\alpha$ cross-linked Hb would substantially reduce or eliminate undesirable physiological side effects. Indeed, those of ordinary skill would not have expected that such modification, which inter alia further increases the circulating life of the rHb, would have such unrelated physiologic benefits.

B. Treatment

The terms "treat" and "treatment" as used herein refer to medical intervention. The terms relate to supplementation of oxygen delivery in vivo, reduction or alleviation of hypovolemia and reduced tissue oxygenation in mammals. The terms also relate to supplementation of existing oxygen-carrying proteins in mammals. For purposes of the present invention, "side-effect" shall be understood to include its generally accepted medical meaning, i.e. an undesirable consequence associated with the administration of a medicinal composition. In the case of certain recombinant hemoglobin-containing solutions, it is believed that such solutions induced non-desirable side effects by indirect or direct alteration of receptor and ligand interactions involved in hemostasis. For example, indirect effects of hemoglobin include the scavenging of nitric oxide which has been implicated in subsequent acetylcholine-mediated stimulation of smooth muscle contraction. Further, it is believed that certain mammals, depending upon the tissue and species, are prone to additional side effects such as esophageal spasm, difficulty in swallowing and elevated blood pressure when certain hemoglobin-based products are administered. In addition, administration of some hemoglobin products results in changes in endothelin receptor interactions and other receptor/ligand populations that lead to changes in vascular bed blood flow and renal glomerular filtration. In each case, the direct action of hemoglobin or its metabolic by-products on hemorphin receptors is believed to be causative of the unwanted side effect. Moreover, hemorphins are believed to play a role in regulating not only blood pressure but also gastrointestinal motility. In view of the foregoing, administration of hemoglobin-based compositions which do not significantly interact with endothelin or hemorphin receptors would be a significant advance.

Particular side-effects associated with certain hemoglobin-based oxygen carriers which are reduced by the conjugation process described herein include nitric oxide-mediated side effects such as increased blood pressure and esophageal spasm, acetylcholine-mediated side effects, alpha-adrenergic-mediated side effects including alpha$_1$-adrenergic and alpha$_2$-adrenergic-mediated side effects such as changes in blood flow within selected vascular beds and renal glomular filtration and endothelin-mediated side effects. Hemoglobin-derived hemorphin-related side effects such as changes in gastrointestinal motility and tone as well as blood pressure and flow have also been described. Polymer conjugation to hemoglobin is believed to inhibit or reduce these side effects also. Combinations of the foregoing side-effects are also reduced by the conjugation process.

C. Oxygen Carrying Proteins

The oxygen-carrying portion of the conjugates of the present invention include mammalian hemoglobins as well as other oxygen-carrying proteins. For example, other suitable proteins include non-mammalian hemoglobins, cyano-hemoglobins and genetically engineered proteins such as serum albumin engineered to include heme binding sites. Additional non-mammalian hemoglobin-type compositions which are suitable for use herein include hemerythrins and myohemerythrins, see K. Dennis et al., 59 Journal of Inorganic Biochemistry 394 (1995), the disclosure of which is incorporated herein by reference.

In preferred aspects of the invention, the oxygen carrying protein is a mammalian-type hemoglobin (Hb). Most preferably, the hemoglobin is a recombinantly-synthesized hemoglobin.

Examples of these preferred genetically engineered hemoglobins are described in U.S. Pat. Nos. 5,028,588 and 5,599,907, the disclosure of each of which is incorporated herein by reference. One such recombinantly-prepared human hemoglobin is available from Somatogen, Inc. of Boulder, Colo. as rHb1.1, a pseudotetrameric di-α-hemoglobin with Asn-108β->Lys and Val to Met changes on the N-termini of the α- and β-chains. This hemoglobin product is synthesized in *Escherichia coli* using an expression vector containing one gene encoding a mutant β-globin with decreased oxygen affinity and one duplicated, tandemly fused α-globin gene. Fusion of the two α-globin subunits increases the half-life of this hemoglobin molecule in vivo by preventing its dissociation into α-β dimers and therefore also reduces renal toxicity. Characteristics of the rHb1.1 are set forth below.

|  | rHb1.1 |
| --- | --- |
| Bohr coefficient | −0.32 |
| $P_{50}$ (torr) | 30 |
| α-chain | di-α |
| α-chain N terminus | Met Leu |
| βchain (β108) | Lys |
| β-chain N terminus | Met His |

See also *Nature*, Vol. 356, Mar. 19, 1992, pp 258–260, the disclosure of which is incorporated herein by reference.

Further alternative hemoglobins include:

1. Cell-free mutant hemoglobins such as those set forth in Table 1 at columns 21–22 of previously incorporated by reference U.S. Pat. No. 5,028,588 supra;
2. Non-naturally occurring hemoglobins such as those described in Table 2 at columns 24–27 of the '588 patent;
3. Additional human hemoglobin variants such as those described in *Hemoglobin: Molecular, Genetic and Clinical Aspects* Bunn, H. F. et al, W. B. Saunders Co. Phila., Pa. (1986), at chapter 10, pp.381–451;
4. *E. coli*-derived hemoglobin such as that described by Vasudevan et al. Mol. Gen. Genet. 226:49(1991) or Poole et al. Proc R. Soc. Lond. B 255: 251 (1994);
5. Protezoan-derived hemoglobins such as those described by Takagi in Current Opin. in Struct Bio. 3:413 (1993); and
6. Yeast-based hemoglobins such as those described by Oshino et al. in Eur. J. Biochem 35:23 (1973) and 39:581 (1973).

The disclosure of each of the foregoing is incorporated herein by reference.

Alternatively, the hemoglobin portion of the conjugates can be obtained from any naturally-occurring, appropriate mammalian source, human or non-human. Human hemoglobin can be obtained from whole human blood which has either been freshly drawn or obtained from "out-dated" supplies from blood banks. Human hemoglobin can also be obtained from placentas or packed erythrocytes obtained from blood donor centers. The hemoglobin can also be obtained from recombinant methods including the establishment of transgenic herds or cells. Such transgenic animals express wild type human, variant human, or mutated human hemoglobins, for example. Non-human hemoglobins include ruminant hemoglobins, such as bovine and/or ovine sources. Porcine hemoglobins are also of use. Specific mammalian species specific hemoglobins are also contemplated. Pharmaceutically-acceptable solutions containing mixtures of various types of Hb conjugated to the poly (alkylene oxides) are also contemplated. The hemoglobin portion can account for about 20–80 percent of the weight of the conjugates. It is also contemplated that the hemoglobin portion of the conjugate can be inter- or intra-molecularly cross-linked to form octamers by recombinant or chemical means.

In a preferred embodiment, the conjugates include poly (alkylene oxide)-modified hemoglobins prepared in a manner such as that described in the above-mentioned patents directed to Hb-polymer conjugates supra (U.S. Pat. Nos. 5,234,903; 5,386,014; 5,312,808 and 5,478,805) previously incorporated by reference herein. It will be understood that the preferred poly(alkylene oxide)-recombinant hemoglobin (PAO-rHb) conjugates are preferably administered in physiologically-acceptable solutions.

The conjugate is preferably formed by covalently bonding a hydroxyl terminal of the poly(alkylene oxide) and the free amino groups of lysine residues of the hemoglobin. See, for example, the aforementioned U.S. Pat. No. 5,234,903, which discloses mPEG-succinimidyl carbonate-Hb conjugates. Other art-recognized methods of conjugating the polymers with the rHb or other oxygen-carrying proteins, such as by via an amide or ester linkage, are also suitable for use with the present invention. While epsilon amino group modifications of hemoglobin lysines are preferred, other conjugation methods are also contemplated. Covalent linkage by any atom between the hemoglobin and polymer is possible. Moreover, non-covalent conjugation such as lipophilic or hydrophilic interactions are also contemplated. Moreover, polyethylene glycol-based liposomes containing either Hb alone or as a PAO-Hb conjugate are also contemplated.

Additional examples of activated polymers which are suitable for covalently conjugating the oxygen carrying proteins are described in commonly assigned U.S. Pat. Nos. 5,349,001; 5,321,095; 5,324,844 and 5,605,976 as well as PCT Publication Numbers WO95/11924 and WO96/00080, the disclosure of each of which is incorporated herein by reference.

Although the preferred conjugates used herein include poly(alkylene oxides), alternative non-antigenic polymeric substances are also useful. Those of ordinary skill in the art will realize that the foregoing is merely illustrative and not intended to restrict the type of non-antigenic polymer or covalent linkage which is suitable for use herein.

D. Polymer Portion of Conjugate

The conjugates preferably include polyethylene glycol (PEG) as the poly(alkylene oxide). The poly(alkylene oxides) include monomethoxy-polyethylene glycol, polypropylene glycol, block copolymers of polyethylene glycol and polypropylene glycol and the like. The polymers can also be distally capped with $C_{2-4}$, alkyls instead of monomethoxy groups.

To be suitable for use herein, the poly(alkylene oxides) must be soluble in water at room temperature. Poly(alkylene oxide) strands having a (number average) molecular weight of from about 200 to about 100,000 Daltons can be used. For example, preferable PAO's have molecular weights of from about 1,000 to about 30,000 while PAO's having a molecular weight of from about 2,000 to about 25,000 are more preferred. Some particularly preferred conjugates of the present invention include poly(alkylene oxide) strands having a molecular weight of about 5,000 Daltons.

E. The Oxygen-Carrying Protein Polymer Conjugates

The conjugate substituents are typically reacted under conditions which are appropriate to effect conjugation of the polymer and hemoglobin yet retain the ability of the hemoglobin or hemoglobin-like substance to transfer oxygen. The reactants are preferably combined under conditions which include a several-fold molar excess of the polymeric substance over the hemoglobin. The reactions are carried out at temperatures of from about 0 to about 25° C. over time periods ranging from a few minutes to as long as 12 hours. Following the conjugation reaction, the desired product is recovered using known techniques and purified using column chromatography or similar apparatus, if necessary.

By controlling the molar excess of the polymer reacted with the hemoglobin, the artisan can tailor the number of polymeric strands attached. The oxygen-carrying protein-substantially non-antigenic polymer conjugate preferably comprises a plurality of substantially non-antigenic polymer strands. For purposes of the present invention, "plurality" shall be understood to mean more than one strand, preferably at least two substantially non-antigenic polymer strands, and more preferably at least about five substantially non-antigenic polymer strands per oxygen-carrying protein. In one aspect of the invention, conjugates containing an average of around 11 strands of mPEG per Hb molecule have been made by reacting about a 15 to 20-fold molar excess of an activated mPEG with recombinant hemoglobin.

The hemoglobin conjugates preferably have a molecular weight of at least about 85,000 Daltons. More preferably, the conjugates have a molecular weight of at least about 10,000 Daltons. Most preferred conjugates have a molecular weight of at least about 120,000 Daltons. The degree of substitution and molecular weight of the conjugates can be varied according to the needs of the artisan. The conjugates, however, should preferably include sufficient size, weight and steric hindrance so as to minimize nephrotoxic effects. Within these parameters, another aspect of the invention includes a substantially non-tissue penetrating hemoglobin-based formulation. The formulation includes a hemoglobin conjugated with or encapsulated in a suitable carrier such as a substantially non-antigenic polymer or liposome. The conjugates or encapsulates have a molecular weight of at least about 120,000 daltons and preferably at least about 130,000 daltons.

F. Hemoglobin-Conjugate Solutions

The amount of conjugates contained in the solution can be in a range of about 0.2–40 wt %; solutions containing about 2–20 are preferred and solutions containing about 4–10 wt % are most preferred. Such solutions are capable of delivering conjugates having an in vivo half life of at least 2 hours, preferably, at least 6–18 hours and most preferably at least 12–20 hours in mammals. Preparations having in vivo half lives of about 40–60 hours in mammals are also contemplated using additional numbers of polymer strands and/or higher molecular weights of polymer. Preferably, the oxygen-carrying protein-substantially non-antigenic polymer conjugate has a circulating half-life of from about 10 to about 70 hours in the mammal. More preferably, the oxygen-carrying protein-substantially non-antigenic polymer conjugate has a circulating half-life of from about 12 to about 48 hours in the mammal.

Solutions containing oxygen-carrying protein-substantially non-antigenic polymer conjugate preferably has a colloidal osmotic pressure of from about 20 to about 200 milliosmoles and more preferably from about 60 to 150 milliosmoles.

It is to be understood that the specific properties i.e. the half life of the conjugates in vivo will depend upon several factors including the species, sex and weight of the mammal and dosage administered.

G. Amount of Oxygen-Carrying Protein Conjugate Administered and Therapy

In one preferred aspect of the invention, the method of the present invention includes:

a) reacting an oxygen-carrying protein with a substantially non-antigenic polymer to form a oxygen-carrying protein-substantially non-antigenic polymer conjugate; and b) administering the oxygen-carrying protein-substantially non-antigenic polymer conjugate to a mammal in need of the oxygen-carrying protein, whereby a reduction in the side-effects associated with administering the unconjugated oxygen-carrying protein is observed.

The amount of the oxygen-carrying protein-polymer conjugate administered is an amount which is therapeutically sufficient. The maximum dose is the highest dosage that does not cause clinically important side effects. For purposes of the present invention, such side effects in humans include clinically important hypervolemia, iron overload, renal damage, etc. The conjugates are usually administered directly into the bloodstream such as via intravenous infusion or transfusion. In the case of transfusional therapy, the solutions can be administered in amounts ranging up to 70+% of the patient's normal blood volume. It will be understood that the fluids may also contain pharmaceutical necessities such as buffers, preservatives, etc. as such ingredients are utilized in the art.

The amount of the conjugate administered will depend upon several factors. For example, the amount of blood loss, the amount of transfusion necessary, etc. as well as the concentration of the conjugated hemoglobin included in the administered solution all will effect the amount administered. As a general guideline, PAO-Hb conjugates are administered in amounts ranging from 0.24–6.3 g/kg and preferably in amounts ranging from 0.72–2.0 g/kg, based on the Hb portion.

EXAMPLES

The following examples serve to provide further appreciation of the invention but are not meant in any way to restrict the effective scope of the invention.

EXAMPLE 1

Conjugation of Recombinant Hemoglobin to mPEG

In this example, recombinant human hemoglobin obtained from Somatogen, Inc. of Boulder, Colo. as rHb1.1 was conjugated to mono-methoxyPEG 5,000 activated with a succinimidyl carbonate linker (SC-mPEG) using the techniques set forth in commonly-assigned U.S. Pat. No. 5,122, 614, the contents of which are incorporated herein by reference. Following the procedure, $1.56 \times 10^{-3}$ moles of rHb1.1 was reacted with a 10-fold molar excess of the SC-mPEG in a reaction vessel containing water for Injection (WFI) in the presence of a phosphate buffer pH 8.8. The reaction was carried out for about one hour at about 10° C. before being quenched with glycine. Cysteine was added to the reaction vessel, and the resultant conjugate-containing solution was microfiltered and thereafter diafiltrated and concentrated into a formulation buffer having a pH of about 7.6. After pegylation, the PEG-rHb1.1 was passed through membrane cartridges containing Sartorious Q membranes. At the pH used, endotoxins are negatively charged and bind tightly to the positively charged membrane surface while the conjugates pass through. The conjugates were then treated by microfiltration using a 22μ filter. The final solution was determined to have a hemoglobin concentration of about 51 mg/ml; about 3% methemoglobin; $P_{50}$ approximately 20 mm Hg and viscosity of about 4.1 cP (shear rate=525 $S^{-1}$). The endotoxin levels were estimated to be less than 2 Eu/ml.

EXAMPLE II

Comparison of Systemic Hemodynamics Polymer Conjugated Hb Vs. Unconjugated Hb

In this example, the PEG-rHb1.1 conjugates prepared above were compared to unconjugates rHb1.1 in a variety of in vivo tests to demonstrate the ability of polymer conjugation to reduce side-effects. Either the PEG-rHb1.1 or the rHb1.1 was administered via i.v. infusion (0.5 ml/min) to conscious animals until the dosage set forth in the following examples, based on the amount of hemoglobin, was delivered.

In this example, rats were divided into 4 groups. Each group received either rHb1.1 alone or the PEG-rHb1.1 according to the table set forth below:

| Group | Hb- product |
|---|---|
| 1 | rHb1.1 350 mg/kg |
| 2 | rHb1.1 750 mg/kg |
| 3 | PEG-Hb1.1 350 mg/kg |
| 4 | PEG-Hb1.1 750 mg/kg |

All rats were instrumented with pulsed Dopper flow probes and in-dwelling arterial and venous catheters. Seven days were allowed for recovery between surgeries and two days were allowed for recovery between catheter placement and experimentation. All measurements for blood pressure, heart rate and cardiac output were made in conscious animals. Total peripheral resistance (TPR) was calculated as blood pressure divided by cardiac output. The calculated number reflected overall vasal tone, with increases in TPR indicating vasoconstriction and an increase in some (localized) or most (systemic) vascular beds. An average value for each parameter in each group was obtained and graphically plotted The measurements for each parameter are set forth in FIGS. 1a–4b.

Referring now to the figures, the advantages of conjugating the recombinantly-prepared human hemoglobin based oxygen carrier are described.

In FIGS. 1a and 1b, it can be seen that the covalent conjugation of the rHb1.1 to mPEG polymer strands significantly prevented the increase in total peripheral resistance which was caused by the unmodified rHb1.1 protein. This advantage was witnessed essentially immediately after administration and throughout the observation period at both dosage ranges. This result demonstrates that the administration of the conjugates is associated with fewer changes in blood flow patterns from the hemostatic condition. Thus, there is a substantial reduction in the pharmacologic-induced burden with patients receiving conjugated recombinant hemoglobin. The ability to reduce or minimize the expected increases in TPR associated with hemoglobin-based products provides therapeutic advantages especially in clinical settings where increased TPR or vasoconstriction would be detrimental, i.e. in an organ vascular bed where ischemia is in progress, where blood flow in an organ vascular bed is "leaky", or in cardiovascularly compromised patients where increased blood pressure or TPR corresponds to increased cardiac work and possibly cardiac ischemia triggering local necrosis, AV block or even fibrillation.

In FIGS. 2a–2b, it can be seen that the conjugation of the rHb1.1 to the polymer had practically no effect on heart rate. This indicates that the PEG rHb1.1 conjugates have a negligible effect on cardiac activities including blood pressure and that tissues are being sufficiently oxygenated.

In FIGS. 3a–3b, a significant increase in cardiac output was observed with the PEG-rHb1.1, especially at the higher (750/mg/kg) dose. This result, coupled with the fact that the PEG-rHb1.1 did not increase heart rate (discussed supra) indicates that a greater volume of blood flow is being achieved per heart stroke than with the unmodified recombinant hemoglobin product. This represents a significant advantage for those patients with weakened cardiac function. Furthermore, the lack of a direct effect on the heart indicates that the non-cardiac patient will not experience any additional strain on the heart. Similar results are observed with polymer conjugates made with other types of hemoglobin, i.e. bovine, etc.

Finally, in FIGS. 4a–4b, it was observed that the mean arterial pressure measurements in the rats administered the 350 mg/kg dose of PEG-rHb1.1 were slightly lower than those observed with the administration of unconjugated rHb1.1. At the higher dose, i.e. 750 mg/kg, the PEG-rHb1.1 solution demonstrated a greatly reduced mean arterial pressure compared with that observed with unconjugated rHb1.1. Thus, the polymer conjugation of the hemoglobin allows the otherwise expected side effects of increased blood pressure to be avoided or substantially reduced.

EXAMPLES III–VI

In these examples, additional conjugation reactions were carried out. In each case, the example was carried out with a different linker and/or a different molecular weight polymer than that used in Example I. The components of each conjugate are set forth below.

| Example | Activated Polymer | Polymer MW | Apparent Molecular Weight |
|---|---|---|---|
| III | monomethoxy-PEG activated with succinimidyl carbonate | 12,000 | 420 |
| IV | monomethoxy-PEG activated with N-acyl thiazolidine | 5,000 | 350 |
| V | methoxy-capped-branched (U) PEG activated with succinimidyl carbonate | 10,000 | 320 |
| VI | monomethoxy-PEG activated with succinimidyl carbonate | 2,000 | 190 |

In Examples III and VI, the procedure of Example I was repeated except that the molecular weight of the activated polymer was changed.

In Example IV, the thizaolidine-thione activated PEG was prepared as described in Example 1 of the aforementioned, commonly assigned U.S. Pat. No. 5,349,001. In Example V, the branched PEG was prepared as described in Example 3 of commonly-assigned PCT International Patent Application having Publication No. WO95/11924.

In each case, the resultant conjugates are made part of pharmaceutically-acceptable solutions and the polymer-rHb1.1 conjugates are administered to patients in need of a blood substitute. Similar hemodynamic effects are observed after administration.

While there have been described what are presently believed to be the preferred embodiments of the invention, those skilled in the art will realize that changes and modifications may be made thereto without departing from the spirit of the invention. It is intended to claim all such changes and modifications that fall within the true scope of the invention.

What is claimed is:

1. A method for administering an oxygen-carrying protein to a mammal comprising:

a) reacting an oxygen-carrying protein with a substantially non-antigenic polymer to form an oxygen-carrying protein-substantially non-antigenic polymer conjugate; and b) administering said oxygen-carrying protein-substantially non-antigenic polymer conjugate to a mammal in need of treatment with said oxygen-carrying protein-substantially non-antigenic polymer conjugate, wherein said mammal exhibits a substantially reduced elevation in mean arterial blood pressure relative to blood pressure changes exhibited by a mammal treated with said oxygen-carrying proteins in non-conjugated form.

2. The method of claim 1, wherein said oxygen-carrying protein is a hemoglobin.

3. The method of claim 2, wherein said hemoglobin is a cell free mutant hemoglobin.

4. The method of claim 2, wherein said hemoglobin is a naturally-occurring hemoglobin.

5. The method of claim 2, wherein said hemoglobin is a non-naturally occurring hemoglobin.

6. The method of claim 4, wherein said naturally-occurring hemoglobin is human hemoglobin.

7. The method of claim 5, wherein said non-naturally occurring hemoglobin is a variant human hemoglobin.

8. The method of claim 2, wherein said hemoglobin is a bovine hemoglobin.

9. The method of claim 1, wherein said oxygen-carrying protein is selected from the group consisting of eukaryotic or prokaryotic flavo(hemoglobin) proteins, cyano-hemoglobins or hemerythrins capable of carrying oxygen.

10. The method of claim 1, wherein said mammal further exhibits a substantially reduced elevation in total peripheral resistance relative to change in peripheral resistance exhibited by a mammal treated with said oxygen-carrying protein in non-conjugated form.

11. The method of claim 1, wherein said oxygen-carrying protein-substantially non-antigenic polymer conjugate includes at least two substantially non-antigenic polymer strands.

12. The method of claim 1, wherein said substantially non-antigenic polymer comprises a poly(alkylene oxide).

13. The method of claim 12, wherein said poly(alkylene oxide) comprises a polyethylene glycol.

14. The method of claim 1, wherein said oxygen-carrying protein-substantially non-antigenic polymer conjugate has a molecular weight of at least about 85,000 Daltons.

15. The method of claim 14, wherein said oxygen-carrying protein-substantially non-antigenic polymer conjugate has a molecular weight of at least about 120,000 Daltons.

16. The method of claim 12, wherein said poly(alkylene oxide) has a molecular weight of about 1,000 to about 30,000.

17. The method of claim 1, wherein said oxygen-carrying protein-substantially non-antigenic polymer conjugate has a circulating half-life of from about 10 to about 70 hours in said mammal.

18. The method of claim 1, wherein said oxygen-carrying protein-substantially non-antigenic polymer conjugate is in a pharmaceutically-acceptable fluid having a colloidal osmotic pressure of from about 20 to about 200 milliosmoles.

19. The method of claim 2, wherein said hemoglobin is prepared by recombinant or transgenic means.

20. The method of claim 2, wherein said hemoglobin includes an α-globin fusion, N-termini mutations of both α- and β-chains of Val to Met and an Asn-108β->Lys mutation.

21. The method of claim 1 wherein said mammal is a human.

22. A method of increasing cardiac output in a mammal, comprising administering an effective amount of a hemoglobin-based polymer conjugate comprising a hemoglobin and a substantially non-antigenic polymer to said mammal.

23. The method of claim 22, wherein said hemoglobin is a cell free mutant hemoglobin.

24. The method of claim 22, wherein said hemoglobin is a naturally-occurring hemoglobin.

25. The method of claim 22, wherein said hemoglobin is a non-naturally occurring hemoglobin.

26. The method of claim 24, wherein said naturally-occurring hemoglobin is human hemoglobin.

27. The method of claim 25, wherein said non-naturally occurring hemoglobin is a variant human hemoglobin.

28. The method of claim 22, wherein said hemoglobin is a bovine hemoglobin.

29. The method of claim 22, wherein said hemoglobin is selected from the group consisting of eukaryotic or prokaryotic flavo(hemoglobin) proteins, cyano-hemoglobins or hemerythrins capable of carrying oxygen and combinations thereof.

30. The method of claim 22, wherein said hemoglobin-based polymer conjugate includes at least two substantially non-antigenic polymer strands.

31. The method of claim 22, wherein said hemoglobin-based polymer conjugate comprises a poly(alkylene oxide).

32. The method of claim 31, wherein said poly(alkylene oxide) comprises a polyethylene glycol.

33. The method of claim 22, wherein said hemoglobin-based polymer conjugate has a molecular weight of at least about 85,000 Daltons.

34. The method of claim 33, wherein said hemoglobin-based polymer conjugate has a molecular weight of at least about 120,000 Daltons.

35. The method of claim 31, wherein said poly(alkylene oxide) has a molecular weight of about 1,000 to about 30,000.

36. The method of claim 22, wherein said hemoglobin-based polymer conjugate has a circulating half-life of from about 10 to about 70 hours in said mammal.

37. The method of claim 22, wherein said hemoglobin-based polymer conjugate is in a pharmaceutically-acceptable fluid having a colloidal osmotic pressure of from about 20 to about 200 milliosmoles.

38. The method of claim 22, wherein said hemoglobin is prepared by recombinant or transgenic means.

39. The method of claim 22, wherein said hemoglobin includes an α-globin fusion, N- termini mutations of both α- and β-chains of Val to Met and an Asn-108β->Lys mutation.

40. The method of claim 22 wherein said mammal is a human.

41. A method of administering an oxygen-carrying protein to a mammal comprising:

a. reacting an oxygen-carrying protein with a substantially non-antigenic polymer to form an oxygen-carrying protein-substantially non-antigenic polymer conjugate; and b. administering said oxygen-carrying protein-substantially non-antigenic polymer conjugate to a mammal in need of treatment with said oxygen-carrying protein-substantially non-antigenic polymer conjugate, wherein said mammal exhibits a substantially reduced elevation in total peripheral resistance relative to total peripheral resistance exhibited by a mammal treated with said oxygen-carrying protein in non-conjugated form.

42. The method of claim 41 wherein said mammal is a human.

43. A method of increasing cardiac output in a mammal, comprising administering an effective amount of an oxygen-carrying protein-substantially non-antigenic polymer conjugate comprising an oxygen-carrying protein and a substantially non-antigenic polymer to said mammal wherein said mammal exhibits a substantially increased cardiac output relative to that exhibited by a mammal treated with said oxygen-carrying protein in non-conjugated form.

* * * * *